United States Patent [19]

Tomimura

[11] Patent Number: 5,055,403

[45] Date of Patent: Oct. 8, 1991

[54] THERMODURIC AND ACIDURIC PULLULANASE ENZYME AND METHOD FOR ITS PRODUCTION

[75] Inventor: Eijiro Tomimura, Higashikurume, Japan

[73] Assignee: Enzyme Bio-Systems, Ltd., Englewood Cliffs, N.J.

[21] Appl. No.: 602,969

[22] Filed: Oct. 24, 1990

Related U.S. Application Data

[63] Continuation-in-part of Ser. No. 371,360, Jun. 26, 1989, abandoned.

[51] Int. Cl.$^5$ .................. C12N 9/44; C12N 1/20; C12P 19/16; C12P 19/10
[52] U.S. Cl. .................. 435/210; 435/252.5; 435/98; 435/100; 435/101; 435/102; 435/814; 435/832
[58] Field of Search .................. 435/252.5, 832, 100, 435/102, 98, 210, 814, 101

[56] References Cited

U.S. PATENT DOCUMENTS

| | | | |
|---|---|---|---|
| 3,897,305 | 7/1975 | Hurst | 435/96 |
| 4,011,139 | 3/1977 | Horwath et al. | 435/210 |
| 4,560,651 | 12/1985 | Nielsen et al. | 435/95 |
| 4,628,028 | 12/1986 | Katkocin et al. | 435/95 |
| 4,734,364 | 3/1988 | Line et al. | 435/95 |

FOREIGN PATENT DOCUMENTS

| | | | |
|---|---|---|---|
| 0063909 | 11/1982 | European Pat. Off. | 435/210 |
| 0188049 | 7/1986 | European Pat. Off. | 435/210 |

OTHER PUBLICATIONS

Patent Abstracts of Japan, vol. 8 (102)(C-222), May 12, 1984, Japan A-5917986.
Patent Abstracts of Japan, vol. 12 (462)(C-549)(3309), Dec. 5, 1988, Japan A-63185380.
Biotech, Abstracts of Japan, No. 88-02127, J. C. Hunter-Cevera, Word Biotech. vol.(2)(3), 1986.
Inter. Journal of Syst. Bact., vol. 40, pp. 123-125 (1990).
Abstr. of the Annual Meeting of the Am. Soc. Microb., vol. 90, p. 248 (1990).
J. Bacterial., vol. 169, pp. 4302-4307 (1987).
Bergey's Manual of Systematic Bacteriology-vol. 2, Williams and Wilkins, pp. 1122-1123, 1104-1111.

*Primary Examiner*—Ronald W. Griffin
*Assistant Examiner*—Pamela S. Webber
*Attorney, Agent, or Firm*—Rockey and Rifkin

[57] ABSTRACT

A thermoduric and aciduric pullulanase enzyme, and a process for its production from a microorganism designated as *Bacillus naganoensis*. The pullulanase is useful for the production of dextrose and high-maltose syrups from starch hydrolyzates.

9 Claims, No Drawings

1

THERMODURIC AND ACIDURIC PULLULANASE ENZYME AND METHOD FOR ITS PRODUCTION

This is a continuation-in-part of application Ser. No. 07/371,360, filed June 26, 1989.

FIELD OF THE INVENTION

This invention relates to a novel enzyme useful for the hydrolysis of certain carbohydrates and to a method for its production by the bacillus, *Bacillus naganoensis* in an aerobic fermentation.

BACKGROUND OF THE INVENTION

A number of high molecular weight carbohydrates are polymers of glucose in which the glucose units are joined by either alpha-1,6-glucosidic linkages or alpha-1,4-glucosidic linkages. It is of considerable industrial importance to be able to cleave these linkages thereby breaking the large carbohydrate molecules into smaller molecules which are more useful in various applications. The breaking of the glucosidic linkages is frequently carried out by enzymes which are produced by microorganisms.

One group of enzymes known as alpha-amylases cleave the alpha-1,4-glucosidic linkages. The alpha-amylase enzymes are produced by such organisms as *Bacillus licheniformis* and *Bacillus stearothermophilus*. Such enzymes do not cleave the alpha-1,6-glucosidic linkages.

Another class of enzymes, sometimes referred to as glucoamylases, are capable of cleaving both alpha-1,6- and alpha-1,4-glucosidic linkages. These enzymes remove one glucose unit at a time from the nonreducing end of the carbohydrate molecule. While they are capable of hydrolyzing alcha-1,6-glucosidic linkages, they hydrolyze the alpha-1,4-glucosidic linkages much more rapidly.

In the conventional dextrose manufacturing process, starch is hydrolyzed in two stages. In the first step, the starch is liquefied by treatment with an alpha-amylase enzyme at a pH between about 5.5 and 7. The liquefied starch is then saccharified by means of a glucoamylase enzyme operating at a pH between 4 and 5.

When the starch hydrolysis process is carried out at the usual concentration of about thirty percent dry solids, only about ninety-six percent dextrose is formed. One reason why conversion does not proceed appreciably beyond this point is due to the presence of a significant number of oligosaccharides in which at least some of the glucose units are joined by alpha-1,6-bonds. Attempts to obtain greater cleavage of these alpha-1,6-bonds by the addition of increased levels of glucoamylase causes repolymerization of dextrose to oligosaccharides.

Similar problems have arisen when starch is converted to high maltose syrups. Oligosaccharides containing alpha-1,6-bonds between the glucose units are not hydrolyzed by the maltogenic enzymes, resulting in a lower percentage of the desired maltose in the syrup.

In order to overcome these problems, previous workers have suggested adding to the glucoamylase, or other saccharifying enzyme, an enzyme which cleaves the alpha-1,6-linkages. Enzymes described as pullulanases have been used for this purpose. These enzymes are capable of hydrolyzing the alpha-1,6-linkages in the polysaccharide pullulan to give the trisaccharide maltotriose. They do not hydrolyze the alpha-1,4-linkages in pullulan. The first pullulanase described was an enzyme produced by *Klebsiella pneumoniae* (*Aerobacter aerocenes*). Reference to its use in a process for hydrolyzing starch is given in U.S. Pat. No. 3,897,305. However, this enzyme has two drawbacks. It is generally active at a pH of 5.5 to 6 where the activity of glucoamylase is dramatically reduced. In addition, the enzyme is thermolabile and cannot be used at temperatures much above 50° C. In commercial operations, it is preferable to carry out the saccharification reactions at 60° C. or higher in order to reduce the risk of microbial contamination of the substrates.

One pullulanase that has been suggested to overcome the foregoing limitations is extracted from rice by a process disclosed in U.S. Pat. No. 4,734,364. Although this enzyme is more thermoduric and aciduric than the enzyme from *Klebsiella pneumoniae*, it does not retain as much activity as is desired under the normal saccharification reaction conditions. Furthermore, the enzyme is contaminated with other enzymes when first extracted from rice and requires extensive purification before it can be used in the saccharification process.

An additional enzyme which has good thermostability is disclosed in U.S. Pat. No. 4,628,028. This enzyme, derived from *Thermoanaerobium brockii*, was classified as a pullulanase based on its ability to hydrolyze pullulan to maltotriose. However, it is not suitable for use in the dextrose manufacturing process because it hydrolyzes very few of the alpha-1,6-glucosidic linkages in starch (Coleman, et al., *J. Bacteriology*, 169, 4302-07 (1987)).

Another pullulanase which was reported to have improved thermoduric and aciduric properties is produced by the microorganism *Bacillus acidopullulyticus*. This is described in U.S. Pat. No. 4,560,651 and marketed under the trade name PROMOZYME.

We have now discovered a microorganism which produces a pullulanase enzyme that hydrolyzes the alpha-1,6-glucosidic linkages in starch and has even greater thermostability than the one derived from *Bacillus acidopullulyticus*. Furthermore, it shows good activity and stability at the acidic pH conditions normally employed for the saccharification of starch. For these reasons, it can be used successfully with glucoamylase to give increased yields of dextrose. It may also be used in conjunction with maltogenic enzymes to produce maltose syrups with high maltose contents.

SUMMARY OF THE INVENTION

In accordance with the present invention, there is provided a thermoduric, aciduric pullulanase enzyme preparation derived from *Bacillus naganoensis*. This enzyme is capable of retaining at least about fifty percent of its pullulan-hydrolyzing activity when held at 60° C. in an aqueous solution at pH 4.5 in the presence of substrate for 232 hours.

Also provided in accordance with this invention is a biologically pure culture of a microorganism, designated as *Bacillus naganoensis*, having the American Type Culture Collection No. ATCC 53909.

In addition, in accordance with this invention, there is provided a process for the preparation of a pullulanase. This process comprises cultivating a pullulanase-producing strain of *Bacillus naganoensis* in a suitable nutrient medium and then isolating the pullulanase enzyme from the medium.

Further, in accordance with this invention, there is provided a process for preparing dextrose from a starch hydrolyzate which comprises saccharification of the starch hydrolyzate with a glucoamylase and an effective amount of the pullulanase enzyme preparation of this invention.

Finally, in accordance with this invention, there is provided a process for the preparation of a high-maltose syrup from a starch hydrolyzate which comprises saccharification of the starch hydrolyzate with a maltogenic enzyme and an effective amount of the pullulanase enzyme preparation of this invention.

DETAILED DESCRIPTION OF THE INVENTION

The pullulanase of this invention was first obtained from a microorganism isolated from a soil sample collected in the Kiso District of the Nagano Prefecture in Japan. The microorganism was characterized by a variety of tests. Based on these tests, the microorganism has been classified as a species of Bacillus to which we have assigned the name *Bacillus naganoensis*.

Growth characterization. To determine the optimum temperature and pH for growth initiation, the organism was inoculated from a slant culture grown on a plate medium containing (per liter of distilled water) 1 g of yeast extract, 2 g of tryptone (Difco Laboratories, Detroit, Mich.), 1 g of $(NH_4)_2SO_4$, 0.3 g of $KH_2PO_4$, 0.2 g of $MgSO_4 \cdot 7H_2O$, 10 mg of $FeSO_4 \cdot 7H_2O$, 0.2 g of $CaCl_2 \cdot 2H_2O$, 1 mg of $MnCl_2 \cdot 4H_2O$, 20 g of agar and 10 g of amylopectin (pH 4.0) for 40h into tryptic soy broth (Difco) containing 1% soluble starch or into the same medium amended with (per liter) 1 g of $(NH_4)_2SO_4$, 0.3 g of $KH_2PO_4$, 0.2 g of $MgSO_4 \cdot 7H_2O$, 0.2 g of $CaCl_2 \cdot 2H_2O$, 10 mg of $FeSO_4 \cdot 7H_2O$, and 1 mg of $MnCl_2 \cdot 4H_2O$. The pH values of the media were adjusted with 4 N sulfuric acid. Growth was followed by determining values for optical density at 660 nm ($OD_{660}$) Dilutions were made in phosphate-buffered saline (0.85%) to give $OD_{660}$ readings ranging from 0.1 to 0.4.

Biochemical Characterization. Biochemical tests with the isolate were performed by using the procedure of Gordon et al., "The Genus Bacillus", *U.S. Dept. of Agriculture Handbook* 427, U.S. Dept. of Agriculture, Washington, D.C. (1973), except that media were prepared at a pH of 5.5 (adjusted with 0.2 N sulfuric acid). Measurements of pH were used to assess acid production from sugars and organic acid utilization. To determine the fatty acid profile, the isolate was grown in nutrient broth supplemented with 1% starch (pH 5.5) at 33° C. for 24 h. The fatty acids were analyzed by using the procedures of DeBoer and Sasser, Can. J. Microbiol. 32, 796 (1986).

DNA base composition. High-molecular-weight DNA was prepared from lysozyme-treated cells by the method of Maniatis et al., *Molecular Cloning: A Laboratory Manual*, Cold Spring Harbor Laboratory, Cold Spring Harbor, N.Y. (1982). The guanine-plus-cytosine content was determined by thermal denaturation measurements (*Methods Enzymology*, 12, 195–206 (1968).

Pathogenicity testing. The pathogenicity potential of the strain was tested in BALB/c mice as described by Reed and Coggin, Indian J. Microbiol. 29, 37–43 (1989). Cells were grown in tryptic soy broth (pH 5.5.) at 33° C. for 24 h. Direct cell counts were obtained by using a Petroff-Hauser chamber, and 10-fold dilutions of the broth culture were made and introduced into the mice via oral or intraperitoneal routes (eight mice per group). Challenge doses as high as $10^7$ cells were administered. Animals were observed for 21 days and then examined postmortem.

Morphology. Cells of the microorganism were rod shaped (0.5 to 1.0 by 2.1 to 10.0 um) and occurred singly or in chains. The ends of the cells were rounded or square. The isolate was gram positive, as determined by conventional staining techniques. The endospores of this organism were oval and subterminally located and caused the sporgania to swell No parasporal crystals were observed. Colonies were opaque, smooth, glistening, convex and circular with entire margins. Colonies reached 2 to 3 mm in diameter after incubation for 3 days on the plate medium described under Growth chacterization.

Growth characteristics. The isolate did not grow under anaerobic or microaerophilic conditions. Optimum aerobic growth in tryptic soy broth containing 1% soluble starch occurred at 28 to 33° C.; no growth occurred at 20° or 45° C. after 4 days of incubation. Growth took place when the initial pH of the medium was 4.1 to 6.0. The pH optimum varied somewhat depending on the medium. When the organism was grown at 33° C. in tryptic soy broth containing 1% starch, the optimum pH was 5.5; however, the maximum cell density was relatively low ($OD_{660}$, 4.2). When the organism was grown in the same medium supplemented with a mixture of inorganic salts (see Growth characterization), the optimum pH for growth initiation was 4.7 to 5.2 and the $OD_{660}$ increased five fold ($OD_{660}$, 21).

Physiological and biochemical properties. The following tests were negative: motility; hydroylsis of gelatin or casein; utilization of citrate or propionate; growth in the presence of 5% NaCl or 0.02% sodium azide; Voges-Proskauer reaction; indole or dihydroxyacetone production; decomposition of tyrosine or hippurate; lecithinase; anaerobic growth; deamination or phenylalanine; and reduction of methylene blue, nitrate or nitrite. The following tests were positive: catalase; starch hydrolysis; growth in the presence of 2% NaCl; and growth at pH 6. Neither NaCl, KCl, allantoin, nor urate was required for growth. No gas was produced from glucose. The isolate produced acid from the following carbohydrates, but only after at least 14 days of growth: L-arabinose, D-xylose, D-glucose, mannitol and lactose (weakly). No acid was produced from sucrose. The fatty acid composition of the cells was as follows: iso-$C_{16}$, 17 mol%; iso-$C_{15}$, 20 mol%; anteiso-$C_{15}$, 11 mol%; iso-$C_{16}$, 45 mol%; n-$C_{16}$, 1 mol%; iso-$C_{17}$, 2 mol%; and anteiso-$C_{17}$, 4 mol%. No unsaturated fatty acids were detected.

Pathogenic potential. Immediately following injection, mice challenged intraperitoneally with $10^6$ or more cells showed slight to moderate distress, as evidenced by ruffled fur and huddling together of cage occupants. Within 24 h, all mice appeared to recover. No effects were seen in other groups. After the 21-day holding period, animals were sacrificed; no abnormalities were seen at necropsy. We concluded that the isolate was nonpathogenic and nontoxicogenic in mice under the conditions of the test.

Description of *Bacillus naganoensis* sp. nov. *Bacillus naganoensis* (na. ga. no. en' sis. M. L. gen. n. naganoensis; of Nagano, a Japanese Prefecture). Cells are rod shaped (0.5 to 1.0 by 2.1 to 10.0 um) with rounded or square ends and occur singly or in chains. Aerobic metabolism. Nonmotile. Gram positive. The endospores are oval and cause swelling of the sporangia. Parasporal crystals are not formed. Colonies, about 2 to 3 mm in diameter, are opaque, smooth, glistening, convex and circular with entire margins. Moderate acidophile; the pH range for growth is about 4.0 to 6.0. Growth occurs optimally at 28° to 33° C. and does not occur at 20° or 45° C. Produces acid (after >14 days of incubation) from L-arabinose, D-xylose, D-glucose, D-mannitol, and lactose (weakly). No gas is produced from glucose. Starch hydrolysis, catalase and growth in the presence of 2% NaCl are positive. Gelatin hydrolysis, casein hydrolysis, growth in the presence of 5% NaCl, phenylalanine deaminase, lecithinase, indole, Voges-Proskauer reactions, citrate utilization and propionate utilization are negative. Does not decompose tyrosine or hippurate or produce dihydoxyacetone from glycerol. Reduction of methylene blue, reduction of nitrate to nitrite and reduction of nitrite to $NO_2$ are negative. The major fatty acid of the isolate grown in nutrient broth containing 1% starch is iso-$C_{16}$ (about 45 mol%). The guanine-plus-cytosine content is 45±2 mol%. A subculture of B. naganoensis has been deposited in the American Type Culture Collection, Rockville, Md., as strain ATCC 53909. The strain was deposited on May 18, 1989 under the provisions of the Budapest Treaty for deposits of microorganisms for patent purposes. It will be irrevocably, and without restriction or condition, released to the public upon the issuance of a patent.

Characteristics which distinguish B. naganoensis from related bacteria At present, aerobic, endosporeforming, rod-shaped bacteria are classified in the genus Bacillus, Bergey's Manual of Systematic Bacteriology, Vol. 2, Williams and Wilkins Co., Baltimore, Md. (1986), which contains 34 species on the *Approved Lists of Bacterial Names*. Several recently described species are as follows: *Bacillus glucanolyticus*, Alexander et al., Int. J. Syst. Bacteriol., 39, 112 (1989); *Bacillus acidoterrestris*, Deinhard et al., Syst. Appl. Microbiol., 10, 47 (1987); *Bacillus cycloheptanicus*, Deinhard et al., Syst. Appl. Microbiol., 10, 68 (1987); *Bacillus halodentrificans*, Denariaz et al., Int. J. Syst. Bacteriol., 39, 145 (1989); *Bacillus alginolyticus* and *Bacillus chondroirinus*, Nakamura, Int. J. Syst. Bacteriol., 37, 284 (1987); and *Bacillus azotoformans*, Pichinoty et al., Int. J. Syst. Bacteriol., 33, 660 (1983). Only five of these species are similar to *B. naganoensis* in that they are strict aerobes that produce oval spores which cause the sporangium to swell. (*Bacillus acidoterrestris, Bacillus cycloheptanicus, Bacillus clobisporus, Bacillus sch-leoelli and Bacillus schaericus*). *B. cycleheptanicus* and *B. schlegelli* are obligate thermophiles, while *B. globisporus* is a psychrophile; therefore, these organisms differ from *B. naganoensis*. Moreover, *B. sphaericus*, unlike *B. naganoensis*, does not produce acid from D-glucose, L-arabinose, D-xylose, or D-mannitol. *B. acidoterrestris* produces w-cyclohexane fatty acids and thus is distinguishable from *B. naganoensis*.

The fatty acid content of *B. naganoensis* appears to be unique. Kaneda, Bacteriol. Rev., 41, 391-418 (1977), has divided the genus Bacillus into six groups based on the predominant fatty acids and the range of fatty acid chain lengths. *B. naganoensis* produces fatty acids with chains of 14 to 17 carbon atoms, a characteristic of four of the six groups; however, the predominant fatty acid of *B. naganoensis* is iso-$C_{16}$ (approximately 45 mol%). None of the groups of Kaneda have iso-$C_{16}$ as the predominant fatty acid; thus, *B. naganoensis* is novel in its fatty acid composition.

*B. naganoensis* is different from the previously described pullulanase-producing Bacillus strains. Bacillus sp. strain 202-1 is an obligately alkalophilic organism, Nakamura et al., Biochem. Biophys. Acta, 397, 188 (1975); *B. cereus* is a Voges-Proskauer-positive, facultative anaerobe; *B. macerans* and *B. polymyxa* are facultative anaerobes that do not produce oval spores; and *B. stearothermochilus* is an obligate thermophile that does not produce oval spores and does not grow at a pH value less than 6. *B. naganoensis* and "*B. acidopullulyticus*" differ in their ability to cause sporangia to swell and in their ability to reduce nitrate, Jensen et al., Process Biochem., 19, 129 (1984). Furthermore, an analysis of the fatty acids from "*B. acidopullulyticus*" showed that this organism produces fatty acids with chains of 12 to 17 carbon atoms and that the predominant fatty acid is iso-$C_{15}$. This places "*B. acidopullulyticus*" in group E of Kaneda.

When the microorganism is used for the preparation of the pullulanase of this invention, it is grown under aerobic conditions in a medium which contains a soluble starch and maltose as the carbohydrate source, yeast extract, protein and minerals in the growth medium. The microorganism will grow in the presence of glucose at a concentration of 0.5 percent, but its growth is repressed when the concentration of glucose is as high as 0.75 percent. The optimum pH of the fermentation medium for the production of pullulanase is from about 5 to about 6 and the optimum temperature is from about 30° to about 37° C.

The pullulanase produced by the microorganism is exerted into the fermentation medium. This indicates that the pullulanase is an extracellular enzyme. The enzyme is obtained by removing the cells from the fermentation medium by conventional means such as centrifugation or filtration. The enzyme may be concentrated by ultrafiltration or other conventional procedures if desired.

In the following descriptions of the preparation and properties of the pullulanase enzyme, all references to parts and percentages are by weight, unless expressly indicated to be otherwise.

Pullulanase Assay

Pullulanase activity was measured (as glucose) by the release of reducing sugar from pullulan in the presence of enzyme. A solution (0.5 ml) containing one percent pullulan, the enzyme being measured, and acetate buffer adjusted to pH 4.5 is incubated at 60° C. for ten minutes. Enzyme action is then terminated by rapid chilling in an ice bath. Then 3 ml of 0.071 percent weight per volume (w/v) $K_3Fe(CN)_6$ solution is added. Solution is mixed, boiled for five minutes and cooled to room temperature. The absorbance at 373 nm is measured and converted to micromoles reducing sugar (as glucose) by comparison with a standard curve of absorbancy at 373 nm versus glucose concentration for 0.5 ml glucose solutions ranging in concentration from 0 percent to 0.04 percent reacted in an equivalent manner. The observed absorbance is corrected for non-specific absorbance produced by the substrate solution in the absence of enzyme and non-specific absorbance produced by the supernatant broth in the absence of defined substrate. One unit of pullulanase activity is defined as the amount of enzyme required to produce one micromole of reducing sugar (measured as glucose) per minute under the conditions of the assay.

Preparation Of Pullulanase

The Bacillus strain which produces the pullulanase enzyme of the present invention is propagated on a solid substrate prior to its cultivation in a suitable fermentation medium. The compositions of the solid slant medium and the liquid culture medium are given in Table I. The cells are first grown on a slant and then transferred to an initial culture medium. After sixteen hours, they are inoculated to a second culture medium where they are grown for an additional six hours before the cells are transferred into the final production culture medium. The fermentation is typically conducted with aeration at a temperature of from about 30° C. to about 37° C. and at an initial pH from about 5 to about 6. The pullulanase enzyme is secreted into the medium.

After the fermentation has been carried out for from about 24 hours to about 48 hours, cells and other solid debris are removed by centrifugation or filtration. The yield of pullulanase enzyme in the supernatant liquid varies from about 15 to about 30 units per ml. The solution may be concentrated as desired by ultrafiltration or evaporation under reduced pressure.

The culture of the microorganism may be maintained for short-term use in a sporulated state on nutrient agar containing one percent amylopectin. For long-term preservation of the culture, cells may be frozen in 10% w/v glycerol at −70° C. or lyophilized in 12% w/v sucrose or 20% w/v skim milk and then refrigerated.

TABLE I

| Media For Pullulanase Growth | | |
|---|---|---|
| | Slant Medium % w/v | Liquid Culture Medium % w/v |
| Soluble starch | — | 3.0 |
| Maltose | — | 1.0 |
| Yeast Extract | 0.1 | 1.5 |
| Bacto-tryptone | 0.2 | — |
| Polypeptone | — | 1.0 |
| Amylopectin | 1.0 | — |
| $(NH_4)_2SO_4$ | 0.1 | 0.25 |
| $KH_2PO_4$ | 0.03 | 0.13 |
| $MgSO_4.7H_2O$ | 0.02 | 0.05 |
| $CaCl_2.2H_2O$ | 0.02 | 0.06 |
| $MnCl_2.4H_2O$ | 0.0001 | 0.0001 |
| $FeSO_4.7H_2O$ | 0.001 | — |
| Agar | 2.0 | — |
| pH adjusted to | 5.0 | 6.0 |

Temperature Optimum For The Enzyme

The effect of the reaction temperature on the enzyme was determined by performing the standard pullulanase assay (pH 4.5) at various temperatures using 0.1 M acetate buffer. At this pH, the temperature optimum of the enzyme was found to be about 62.5° C.

pH Effect On The Enzyme

The pullulanase activity of the enzyme was determined by performing the pullulanase assay at 60° C. at various pH values (0.1 M acetate buffer). The enzyme showed maximum activity at about pH 5 and showed over 90% of its maximum activity from pH 4.0 to 5.5.

Thermostability Of The Enzyme

In order to study the stability of the enzyme in buffer solution in the absence of substrate, samples of the enzyme were diluted to a concentration of approximately one unit per ml in 0.1 M acetate buffer solution (pH 4.5) and incubated at 60° C. Samples which had incubated for various times were assayed for residual enzymatic activity. The enzyme half-life was 21.6 minutes under these conditions. When the test was repeated in 0.1 M acetate buffer at pH 5.0, the half-life was 49.8 minutes.

When a sample of the commercial pullulanase enzyme PROMOZYME (Novo Laboratories, Wilton, Conn.) from *Bacillus acidopullulyticus* was tested under similar conditions, it had significantly lower half-lives of only 5.9 minutes at pH 4.5 and 14.1 minutes at pH 5.0.

The heat stability of the pullulanase enzyme of this invention was also determined in the presence of a starch hydrolyzate. In this case, the enzyme was diluted to a concentration of a ten dextrose equivalent (D.E.) starch hydrolyzate. The solution was incubated at 60° C. and samples were taken at various times to determine the residual enzymatic activity. The material had a half-life of 232 hours when the reaction was run at pH 4.5. A comparison test was run with the commercial pullulanase enzyme, PROMOZYME, (Novo Labs, Wilton, Conn.). This enzyme produced by *Bacillus acidopullulyticus* had a half-life of approximately 121 hours under the same conditions. These examples clearly show the superior thermostability of the enzyme of this invention.

Hydrolysis Of Pullulan

A 5 percent aqueous solution of pullulan was hydrolyzed by treatment with the enzyme of this invention (1 unit per ml of pullulan solution) for one hour at pH 4.5 and 60° C. The product as determined by paper chromatography was principally maltotriose with small amounts of maltohexaose.

Dextrose Producing Using The Enzyme

A starch hydrolyzate with a D.E. of 18.8 was prepared by hydrolyzing granular corn starch with an alpha-amylase enzyme. To a 30% w/v aqueous solution of starch containing 100 ppm calcium ion was added 2.5 units of the enzyme per gram of starch, dry basis. The alpha-amylase used was G-ZYME® G995 (Enzyme Bio-Systems, Ltd., Englewood Cliffs, N.J.). The mixture (pH 6.0) was heated with stirring at 98° C. for 90 minutes and then cooled.

A solution containing 30% w/v of the 18.8 D.E. starch hydrolyzate was adjusted to pH and heated at 60° C. with a mixture of glucoamylase plus the pullulanase enzyme of this invention. The glucoamylase was a commercial glucoamylase G-ZYME® G990 available from Enzyme Bio-Systems, Ltd. It was used at the rate of 0.2 units per gram of dry substance in the starch hydrolyzate. The pullulanase of this invention was used at the rate of 0.9 unit per gram of dry substance in the starch hydrolyzate. Samples were analyzed for dextrose content by high performance liquid chromatography (HPLC) at various times. A comparative test was performed using the same proportions, except that no pullulanase enzyme was added. The results given in Table II show that the use of pullulanase enzyme of this invention with glucoamylase gives a more rapid production of dextrose and a greater ultimate yield of dextrose than that obtained with glucoamylase alone.

TABLE II

| | Dextrose Production | |
|---|---|---|
| | % Dextrose | |
| Reaction Time (hours) | Glucoamylase | Glucoamylase and Pullulanase |
| 23 | 92.7 | 95.6 |
| 47 | 95.4 | 96.5 |
| 71 | 96.0 | 96.5 |
| 96 | 96.0 | 96.5 |

When preparing dextrose by the saccharification of a starch hydrolyzate with a glucoamylase and the pullulanase enzyme of this invention, the saccharification may be carried out at a pH from about 4.0 to about 6.0 and at a temperature of from about 55° C. to about 65° C.

Maltose Production Using The Enzyme

A solution containing 30 % w/v of a 10 D.E. starch hydrolyzate was adjusted to pH 5.0 and heated at 55° C. with a mixture of a commercial malt extract and pullulanase enzyme of this invention. The malt extract was used at a rate of 0.2 percent by weight of starch hydrolyzate (dry basis). The pullulanase was used at a rate of 0.9 unit per gram dry substance in the starch hydrolyzate. Samples were analyzed for maltose content by HPLC at various times. Comparative tests were run using malt extract alone. The results given in Table III show that the pullulanase enzyme of this invention increases the production of maltose from a starch hydrolyzate when it is saccharified by a maltogenic enzyme. It also shows the superior maltose-producing ability of the pullulanase enzyme of this invention over that of the commercial pullulanase derived from *B. acidopullulyticus*.

TABLE III

| | Maltose Production | | |
|---|---|---|---|
| | | % Maltose | |
| Reaction Time (Hours) | Malt | Malt and B. naganoensis Pullulanase | Malt and B. acidopullulyticus Pullulanase |
| 5 | 49.9 | 50.2 | 49.4 |
| 24 | 55.3 | 62.0 | 58.4 |
| 42 | 56.0 | 66.0 | 61.1 |

When preparing a high-maltose syrup from a starch hydrolyzate by the use of the pullulanase enzyme with a maltogenic enzyme preparation, it is preferable to carry out the saccharification at a pH of from about 4.5 to about 5.5 and at a temperature of from about 55° C. to about 60° C.

Thus, there has been provided, in accordance with this invention, a thermostable pullulanase enzyme, a process for its preparation and processes for preparing dextrose and high maltose syrups using this enzyme. Although the invention has been described in conjunction with specific embodiments thereof, it is evident that many alternatives, modifications and variations will be apparent to those skilled in the art in light of the foregoing description. Accordingly, it is intended to include all such alternatives, modifications, and variations as set forth within the spirit and scope of the appended claims.

What is claimed is:

1. A thermoduric, aciduric pullulanase enzyme preparation derived from *Bacillus naganoensis*, said enzyme being capable of retaining at least about fifty percent of its pullulan-hydrolyzing activity when held at 60° C. in an aqueous solution at pH 4.5 in the presence of substrate for 232 hours.

2. Pullulanase enzyme preparation of claim 1, wherein the strain of *Bacillus naganoensis* is strain ATCC No. 53909.

3. The pullulanase enzyme preparation of claim 2 having a maximum pullulanase-hydrolyzing activity at pH of about 5 when measured at 60° C.

4. The pullulanase enzyme preparation of claim 2 having a maximum pullulanase-hydrolyzing activity at a temperature of about 62.5° C. when measured at pH of 4.5.

5. A biologically pure culture of the microorganism, *Bacillus naganoensis* having all of the identifying characteristics of American Type Culture Collection No. ATCC 53909.

6. A process for the preparation of a pullulanase enzyme which comprises cultivating a pullulanase-producing strain of *Bacillus naganoensis* in a suitable nutrient medium and then isolating the pullulanase from the medium.

7. The process of claim 6, wherein the strain of *Bacillus naganoensis* is strain ATCC No. 53909.

8. The process of claim 6, wherein the nutrient medium contains soluble starch, maltose, yeast extract, protein and minerals.

9. The process of claim 6, wherein the pH is from about 5 to about 6 and the temperature is from about 30° C. to about 37° C.

* * * * *